United States Patent
Silverberg et al.

(10) Patent No.: US 7,189,221 B2
(45) Date of Patent: Mar. 13, 2007

(54) METHODS FOR THE TREATMENT OF A NORMAL PRESSURE HYDROCEPHALUS

(75) Inventors: Gerald Silverberg, Stanford, CA (US); Tom Saul, El Granada, CA (US); Dawn McGuire, Berkeley, CA (US); Marvin Sussman, Miami, FL (US)

(73) Assignee: Integra Life Sciences Corporation, Plainsboro, NJ (US)

( * ) Notice: Subject to any disclaimer, the term of this patent is extended or adjusted under 35 U.S.C. 154(b) by 744 days.

(21) Appl. No.: 10/382,086

(22) Filed: Mar. 4, 2003

(65) Prior Publication Data

US 2004/0068221 A1   Apr. 8, 2004

Related U.S. Application Data

(63) Continuation-in-part of application No. 10/138,082, filed on May 3, 2002, now Pat. No. 6,575,928, which is a continuation of application No. 09/189,037, filed on Nov. 10, 1998, now Pat. No. 6,383,159, said application No. 10/382,086 and a continuation-in-part of application No. 10/224,046, filed on Aug. 19, 2002, now abandoned.

(51) Int. Cl.
  *A61M 31/00*   (2006.01)
(52) U.S. Cl. .......................................... 604/500; 604/9
(58) Field of Classification Search ............. 604/8–10, 604/500, 503, 505, 506, 28, 30
  See application file for complete search history.

(56) References Cited

U.S. PATENT DOCUMENTS 3,111,125 A    11/1963   Schulte
3,886,948 A    6/1975   Hakim
3,889,687 A    6/1975   Harris et al.
3,913,587 A    10/1975  Newash
3,985,140 A    10/1976  Harris
4,156,422 A    5/1979   Hildebrandt et al.
4,261,341 A    4/1981   Hakim et al.
4,375,816 A    3/1983   Labianca
4,377,169 A    3/1983   Banks
4,385,636 A    5/1983   Cosman
4,432,853 A    2/1984   Banks
4,532,932 A    8/1985   Batty, Jr.

(Continued)

FOREIGN PATENT DOCUMENTS

EP    0 115 973 B1    8/1984

(Continued)

OTHER PUBLICATIONS

Abbott, KH, MD, et al., The Central Nervous System, *JAMA* Jul. 6, 1963, 104-115.

(Continued)

*Primary Examiner*—Kevin C. Sirmons
*Assistant Examiner*—Bhisma Mehta
(74) *Attorney, Agent, or Firm*—Caesar, Rivise, Bernstein, Cohen, & Pokotilow, Ltd.

(57) ABSTRACT

Normal pressure hydrocephalus is treated by removing cerebralspinal fluid (CSF) from a CSF space of a patient. In particular, CSF is drained while pressure within the CSF space remains within an expected normal range for the patient.

34 Claims, 13 Drawing Sheets

U.S. PATENT DOCUMENTS

| | | |
|---|---|---|
| 4,540,400 A | 9/1985 | Hooven |
| 4,551,128 A | 11/1985 | Hakim et al. |
| 4,557,721 A | 12/1985 | Hooven |
| 4,560,375 A | 12/1985 | Schulte et al. |
| 4,576,035 A | 3/1986 | Hooven et al. |
| 4,595,390 A | 6/1986 | Hakim et al. |
| 4,598,579 A | 7/1986 | Cummings et al. |
| 4,601,721 A | 7/1986 | Kamerling |
| 4,605,395 A | 8/1986 | Rose et al. |
| 4,610,658 A | 9/1986 | Buchwald et al. |
| 4,627,832 A | 12/1986 | Hooven et al. |
| 4,631,051 A | 12/1986 | Harris |
| 4,673,384 A | 6/1987 | Marion |
| 4,675,003 A | 6/1987 | Hooven |
| 4,676,772 A | 6/1987 | Hooven |
| 4,681,559 A | 7/1987 | Hooven |
| 4,705,499 A | 11/1987 | Hooven |
| 4,714,458 A | 12/1987 | Hooven |
| 4,714,459 A | 12/1987 | Hooven |
| 4,729,762 A | 3/1988 | Doumenis |
| 4,741,730 A | 5/1988 | Dormandy, Jr. |
| 4,769,002 A | 9/1988 | Hooven |
| 4,776,838 A | 10/1988 | Sainte-Rose et al. |
| 4,781,672 A | 11/1988 | Hooven |
| 4,787,886 A | 11/1988 | Cosman |
| 4,850,955 A | 7/1989 | Newkirk |
| 4,861,331 A | 8/1989 | East et al. |
| 4,867,740 A | 9/1989 | East |
| 4,885,002 A | 12/1989 | Watanabe et al. |
| 4,904,237 A | 2/1990 | Janese et al. |
| 4,931,039 A | 6/1990 | Coe et al. |
| 4,933,156 A | 6/1990 | Quay et al. |
| 4,950,232 A | 8/1990 | Ruzicka et al. |
| 5,039,511 A | 8/1991 | Quay et al. |
| 5,069,663 A | 12/1991 | Sussman |
| 5,167,615 A | 12/1992 | East et al. |
| 5,334,315 A | 8/1994 | Matkovich et al. |
| 5,336,166 A | 8/1994 | Sierra |
| 5,368,556 A | 11/1994 | Lecuyer |
| 5,372,573 A | 12/1994 | Habib |
| 5,385,541 A | 1/1995 | Kirsch et al. |
| 5,385,582 A | 1/1995 | Ommaya |
| 5,387,188 A | 2/1995 | Watson |
| 5,425,368 A | 6/1995 | Brandt |
| 5,437,627 A | 8/1995 | Lecuyer |
| 5,458,606 A | 10/1995 | Cohen et al. |
| 5,462,667 A | 10/1995 | Wollinsky et al. |
| 5,601,985 A | 2/1997 | Trojanowski et al. |
| 5,643,194 A | 7/1997 | Negre |
| 5,643,195 A | 7/1997 | Drevet et al. |
| 5,660,200 A | 8/1997 | Paes |
| 5,683,357 A * | 11/1997 | Magram ............ 604/8 |
| 5,980,480 A * | 11/1999 | Rubenstein et al. ........ 604/9 |
| 6,264,625 B1 | 7/2001 | Rubenstein et al. |
| 6,383,159 B1 | 5/2002 | Saul et al. |
| 6,575,928 B2 | 6/2003 | Saul et al. |
| 6,875,192 B1 | 4/2005 | Saul et al. |
| 2005/0010159 A1* | 1/2005 | Reich et al. ............ 604/8 |
| 2005/0038371 A1* | 2/2005 | Reich et al. ............ 604/9 |

FOREIGN PATENT DOCUMENTS

| | | |
|---|---|---|
| EP | 0 117 695 B1 | 9/1984 |
| EP | 0 421 558 B1 | 4/1991 |
| EP | 0 478 842 A1 | 4/1992 |
| EP | 0 798 011 A1 | 10/1997 |
| EP | 0 798 012 B1 | 10/2001 |
| FR | 2 354 103 | 6/1978 |
| FR | 2 685 206 A1 | 6/1993 |
| FR | 2 705 574 A1 | 12/1994 |
| SE | 8801516 A | 5/1989 |
| SU | 1297870 A1 | 3/1987 |
| WO | WO 96/28200 | 9/1996 |
| WO | WO 98/02202 | 1/1998 |
| WO | WO 03/068049 A2 | 8/2003 |

OTHER PUBLICATIONS

Barnett, GH, MD et al., Normal Pressure Hydrocephalus in Children and Young Adults, *Neurosurgery*, (1987) vol. 20. No. 6. 904-907.

Boon, AJW, et al., Does CSF Outflow Resistance Predict the Response to Shunting in Patients with Normal Pressure Hydrocephalus? *Acta Neurochir* (1988) (Suppl) 71:331-333.

Boon, AJW, et al., Dutch Normal-Pressure Hydrocephalus Study: Prediction of Outcome After Shunting by Resistance to Outflow of Cerebrospinal Fluid, *J. Neurosurg* (1997) 87:687-693.

Boon, AJW, et al. Dutch Normal-Pressure Hydrocephalus Study: The Role of Cerebrovascular Disease,*J. Neurosurg* 90:221-226, 1999.

Chapman, PH, MD, et al. The Relationship between Ventricular Fluid Pressure and Body Position in Normal Subjects and Subjects with Shunts: A Telemetric Study, *Neurosurgery*. (1990) vol. 26, No. 2, 181-189.

Chen, IH, et al., Effectiveness of Shunting in Patients with Normal Pressure Hydrocephalus Predicted by Temporary, Cntrolled-Resistance, Continuous Lumbar Drainage: A Pilot Study. *J. Neurology, Neurosurgery, and Psychiatry* (1994) 57:1430-1432.

Clarfield, AM, MD. et al., Normal-Pressure Hydrocephalus: Saga or Swamp? *JAMA*, Nov. 10, 1989, vol. 262, No. 18, 2592-2593.

Condon, BR, et al., A Quantitative Index of Ventricular and Extraventricular Incracranial CSF Volumes Using MR Imaging, *J. Computer Assisted Tomography* 10(5): 784-792, Sep./Oct. 1986.

Condon, B., et al., MR Relaxation Times of Cerebrospinal Fluid, *J. Computer Assisted Tomography*, 11(2):203-207, Mar./Apr. 1987.

Damasceno, BP, et al., The Predictive Value of Cerebrospinal Fluid Tap-Test in Normal Pressure Hydrocephalus, *Arq Neurosiquiatr* 199755(2):179-185.

Friedland, RP, MD. 'Normal'-Pressure Hydrocephalus and the Saga of the Treatable Dementias, *JAMA* Nov. 10, 1989, vol. 262, No. 18, 2577-2581.

Golomb, J. et al., Alzheimer's Disease Comorbidity in Normal Pressure Hydrocephalus: Prevalence and Shunt Response. *J. Neurol, Neurosurgery, and Psychiatry* 2000, 68:778-781.

Adams et al., "Disturbances of cerebrospinal fluid circulation, including hydrocephalus and meningeal reactions," *Principles of Neurology*, Fourth Edition, Chapter 30, 1989, pp. 501-502.

Adams, R.D. et al., "Symptomatic occult hydrocephalus with 'normal' cerebrospinal-fluid pressure" *The New England Journal of Medicine*, vol. 273, No. 3, pp. 117-126 (Jul. 15, 1965).

Appenzeller et al., Treatment of parenchymatous degeneration of the brain by ventriculo-atrial shunting of the cerebrospinal fluid, *Journal of Neurosurgery*, vol. XXVI, pp. 478-482, (Jan.-Jun. 1967).

Arai et al., "Tau in cerebrospinal fluid: a potential diagnostic marker," *Ann. Neurology*, vol. 38, 1995, pp. 649-652.

Bannister et al., "Isotope encephalography in the diagnosis of dementia due to communicating hydrocephalus" *The Lancet*, pp. 1014-1017, (Nov. 11, 1967).

Bush et al., "Beta A-4 amyloid protein and its precursor in Alzheimer's disease," *Pharmac. Tera.*, vol. 56, 1992, pp. 97-117.

Frankel et al., "High affinity binding of monoclonal antibodies to the sequential epitope EFRH of $\bar{y}$-amyloid peptide is essential for modulation of fibrillar aggregation" J. Immunol. (1999) 95:136-142.

Frankel et al., "Modulation of Alzheimer's $\bar{y}$-amyloid neurotoxicity by site-directed single-chain antibody" J. Immunol. (2000) 106:23-31.

Graff-Radford et al., "Normal-pressure hydrocephalus" *Neurol.* (1986) 43:940-942.

Gustafson et al., "Recovery in hydrocephalic dementia after shunt operation" *J. Neurol. Neurosurg. Psych.* (1978) 41:940-947.

Hakim et al., "The special clinical problem of symptomatic hydrocephalus with normal cerebrospinal fluid pressure. Observations on cerebrospinal fluid hydrodynamics" *J. Neurol. Sci.* (1965) 2:307-327.

Ko et al., "Cerebrospinal fluid control system" Proceedings of the IEEE, vol. 76, No. 9, pp. 1226-1235, Sep. 1988.

Martinez et al., "Relationship of interleukin-1 beta and beta$_2$-microglobulin with neuropeptides in cerebrospinal fluid of patients with dementia of the Alzheimer type," *J. Neuroimmunology*, vol. 48, 1993, pp. 235-240.

Mataró et al., "Cognitive changes after cerebrospinal fluid shunting in young adults with spina bifida and assumed arrested hydrocephalus" *J. Neurol. Neurosurg. Psych.* (2000) 68:615-621.

Nakamura et al., "Amyloid beta protein levels in cerebrospinal fluid are elevated in early-onset Alzheimer's disease," *Ann. Neurology*, vol. 36, 1994, pp. 903-911.

Ono et al., "Formation of amyloid-like substance from beta-2-microglobulin in vitro. Role of serum amyloid P component: a preliminary study," *Nephron.* vol. 66, 1994, pp. 404-407.

Salmon, James H., "Senile and presenile dementia" *Geriatrics* (Dec. 1969) 24 (12) : 67-72.

Shenkin et al., "Ventricular shunting for relief of senile symptoms" *JAMA* (1973) 225(12):1486-1489.

Skinhøj Erik, "Determination of regional cerebral bloodflow in man" Head injury conference proceedings, held at the University of Chicago Center for Continuing Education with Joseph P. Evans as host, No. 34, pp. 431-438.

Solomon et al., "Disaggregation of Alzheimer ÿ-amyloid by site-directed mAb" Proc. Natl. Acad. Sci. (1997) 94:4109-4112.

Solomon et al., "Monoclonal antibodies inhibit in vitr o bibrillar aggregation of the Alzheimer ÿ-amyloid peptide" Proc. natl. Acad. Sci. (1996) 93:452-455.

Vanneste et al., "Shunting normal-pressure hydrocephalus: Do the benefits outweigh the risks?" *Neurol.* (1992) 42:54-59.

Vorstrup et al., "Cerebral blod flow in patients with normal-pressure hydrocephalus before and after shunting" *J. Neurol.* (1987) 66:379-387.

Williams et al., "Evaluation of shunt function in patients who are never better, or better than worse after shunt surgery for NPH" *Acta Neurochir.* (1998) 71:368-370.

Holodny, Al, et al. Focal dilation and paradoxical collapse of cortical fissures and sulci in patients with normal-pressure hydrocephalus, *J. Neuorosurg.* vol. 89,1998 89:742-747.

Kaye, JA et al., Plasticity in the Aging Brain, *Arch. Neurol.*, vol. 47, Dec. 1990, 1336-1341.

Langfitt, TW, MD, Clinical Methods for Monitoring Intracranial Pressure and Measuring Cerebral Blood Flow, Clinical Neurosurgery, Proc. of the Congress of Neurological Surgeons, Vancouver, BC 1974, Pub. by The Williams & Wilkins Co., 1975, 302-320.

Magnaes, B. MD, Body Position and Cerebrospinal Fluid Pressure, *J. Neurosurg* vol. 44, Jun. 1976, 698-705.

Medco Forum, "CSF flow regulation: The future of CSF shunting" (Apr. 1998) vol. 3, 2 pages total.

Mogilner, A., et al. Hydrocephalus: Does Coexistent AlzheimerO's Disease Affect Outcome? http://cnshomc.org/abstracts/abst.

Rubenstein, E., Relationship of Senescence of Cerebrospinal Fluid Circulatory System to Dementias of the Aged, *The Lancet* vol. 351, Jan. 24, 1998. 283-285.

ORBIS-Sigma® Valve Unit, Nitinol Medical Technologies, Inc. Boston, MA 02210 (formerly Cordis).

Product Brochure for "The Future of CSF Shunting. The Phoenix Diamond™ Valve" Phoenix Corp., P.O. Box 80390, Valley Forge, PA 19426 2 pages total.

Czosnyka, et al. "Posture related Overdrainage: Comparison of the Performance of 10 Hydrocephalus Shunts in Vitro" *Neurosurgery* (1998) 42(2):327-334.

Gower, M.D., et al., "Sterile Shunt Malfunction", *J. Neurosurgery* (1984) 61:1079-1084.

Sainte-Rose, et al., "A new Approach in the Treatment of Hydrocephalus", *J. Neurosurg.* vol. 66, Feb. 1987 pp. 213-226.

Williams, MA, et al. "Comparison of Pcsf Monitoring and controlled CSF Drainage Diagnose Normal Pressure Hydrocephalus", Acta Neurochir (1998) (Suppl) 71:328-330.

Wood, M.D. editor Neurobiology of Cerebrospinal Fluid, "Body Position and CSF Pressure" Chapter 39, Plenum Press, N.Y. pp. 630-641.

* cited by examiner

METHODS FOR THE TREATMENT OF A NORMAL PRESSURE HYDROCEPHALUS

CROSS-REFERENCES TO RELATED APPLICATIONS

The present application is a continuation-in-part of application. Ser. No. 10/138,082, filed on May 3, 2002, now U S. Pat. No. 6,575,928, which was a continuation of application Ser. No. 09/189,037, filed on Nov. 10, 1998, now U.S. Pat. No. 6,383,159. The present application is also a continuation-in-part of application Ser. No. 10/224,046, filed on Aug. 19, 2002, now abandoned. The full disclosures of each of these application a are incorporated herein by reference.

BACKGROUND OF THE INVENTION

1. Field of the Invention

The present invention relates generally to medical methods. More particularly, the present invention relates to improved methods for treating normal pressure hydrocephalus (NPH) by removing cerebrospinal fluid (CSF) from a CSF space of a patient while pressure within the CSF space remains within a normal range.

NPH is a well recognized but relatively rare condition involving an enlargement of the ventricles with little or no increase on pressure in the ventricles. It is primarily a condition of the aged although it can but rarely occurs in the young. It is characterized by a "triad" of symptoms including apraxia of gait, urinary incontinence, and dementia. Although this triad of symptoms characterizes this disorder, it is not necessary for all three symptoms to be present to make the diagnosis. In contrast to hydrocephalus in infants and an adult-onset form which are characterized by ventricular enlargement with excessive CSF volume and elevated intracranial pressures, NPH is commonly thought to be associated with "normal" CSF pressures. Such conventional wisdom, however, is misleading since NPH is typically associated with normal CSF pressures during the day and intermittently increased CSF pressure at night.

Despite the quite different etiologies, NPH is treated in the same manner as other forms of hydrocephalus, i.e., by the implantation of a ventricular shunt which drains CSF during periods of elevated CSF pressure. Treatment of NPH using conventional pressure-responsive shunts has proven to be only partially effective. When all three symptoms are present, one or more may not respond to treatment at all or respond to different degrees. In particular, such shunt implantation procedures will sometimes clear or reduce the symptoms of urinary incontinence and apraxia of gait, but will seldom improve or stabilize the patient's dementia. Use of these shunts also carries with it the significant and life threatening risk of over drainage complications.

For these reasons, it would be desirable to provide improved methods for treating NPH, where such methods would not only be able to improve the patient's condition relative to incontinence and apraxia of gait, but would also be more effective in treating the dementia associated with this disorder than are prior methods of treating NPH. In particular, it would be desirable to utilize improved shunts and other CSF removal devices which can remove and drain CSF under different flow conditions and patterns than those provided by prior CSF shunts utilized to treat NPH. At least some of these objectives will be met by the invention as described and claimed hereinafter.

2. Description of Background Art

Normal pressure hydrocephalus NPH is commonly treated by the implantation of traditional ventriculoperitoneal, lumboperitoneal or similar shunts which drain CSF from the ventricles or lumbar subarachnoid space at differential pressures, described later, typically at or above 35 mm $H_2O$. Commercially available ventricular shunts which have been used for treating NPH include fixed pressure valves such as the ball-in-cone, slit, miter or diaphragm valves, fixed pressure valves that include a siphon-limiting device, gravity-compensating device or flow regulation or adjustable-pressure valves such as the Codman Hakim Programable and Medronic Strata valves. Even the adjustable pressure valves, which are adjusted non-invasively using a magnetic programmer, do not automatically adjust to the patient's changing requirements. Because of their operational pressure ranges, it would not be expected that these shunts would drain CSF during periods when the pressure in the patient's ventricle is generally normal, e.g., in a range from −170 mm $H_2O$ to 200 mm $H_2O$. A comparison of the pressure-flow performance of a number of commercially available hydrocephalus shunt devices is presented in Czosnyka et al. (1998) *Neurosurgery* 42: 327–334. A shunt valve having a three-stage pressure response profile is sold under the Orbis-Sigma® tradename by Nitinol Medical Technologies, Inc., Boston, Mass. 02210 (formerly by Cordis) now manufactured and marketed by Integra Neurosciences, Inc. (Plainsboro, N.J.).

Recently, a promising treatment for Alzheimer's disease (AD) and other conditions associated with CSF toxins has been proposed. The proposed treatment relies on removal of CSF from the CSF space in order to both reduce the concentration of the suspected toxic substances and to promote turnover of the CSF and transport of other normal substances which may become toxic or deleterious under conditions of deficient CSF removal and turnover. Such CSF removal may be achieved in either of two ways. First, drainage can be provided by implanting a shunt which drains CSF at a substantially continuous flow rate so long as pressure in the CSF space remains within the normal range. Such pressure-responsive ventriculoperitoneal shunts are described in U.S. Pat. No. 6,383,159, and are available from Eunoe, Inc., Redwood City, Calif. under the COGNIshunt® tradename. Alternatively, target volumes of the CSF may be removed intermittently during predetermined time periods, as generally described in co-pending application Ser. No. 10/224,046, filed on Aug. 19, 2002, commonly assigned herewith. Use of such low and continuous flow shunts and/or such intermittent, volumetric-removal shunts for the treatment of NPH has not heretofore been proposed.

Conventional shunts used in the treatment of NPN and for high pressure forms of hydrocephalus are designed to control intracranial pressure (ICP). Such shunts must therefore be chosen, in the case non-adjustable shunts, or adjusted, in the case of adjustable shunts, to operate at a particular pressure control point (i.e., opening pressure). In this case pressure is being controlled and the flow through the shunt necessary to maintain this pressure point is variable and unknown. For this reason it is often the case that the control point of the shunt is mismatched to the patient and either too much or too little CSP is drained. These conditions are known as overdrainage and underdrainage, respectively. Overdrainage, if untreated, can have severe and life threatening consequence. Since brain anatomy may be changed, overdrainage leads to the ventricles undergoing a significant reduction in volume, becoming slit-like. They may actually close down around the holes of the ventricular catheter causing intermittent or permanent shunt obstruction. The cortical surface may move downward (due to a reduction in the size of the ventricles) which leads to a tearing of the bridging veins with concomitant development of subdural fluid collections such as subdural hematomas. Underdrainage, on the other hand leads to a lack of efficacy. The present invention postulates that NPH is not a fundamentally disease of elevated pressure, but a disease of poor CSF circulation and turnover. A shunt, as defined in the present invention, designed to provide for a known and safe low flow, would protect against both over and underdrainage while therapy to the NPH patient.

BRIEF SUMMARY OF THE INVENTION

Improved methods for treating normal pressure hydrocephalus NPH comprise draining CSF from a patient's CSF space (as defined hereinafter) under normal pressure conditions (also as defined hereinafter). It is believed that a low flow, continuous CSF removal protocol not only reduces or eliminates the symptoms of urinary incontinence and apraxia of gait associated with NPH but will also stabilize or improve an NPH patient's condition of dementia. In particular, it is believed that NPH patients will show a statistically significant improvement in reduction or stabilization of dementia when compared with patients treated using conventional shunting technology.

All patients treated according to the methods of the present invention will be suffering from NPH, as defined hereinafter. Individual patients being treated, however, may also be suffering concurrently from other conditions, such as Alzheimer's disease (AD), although a significant number of the patients will not be suffering from AD. The present invention is intended to treat AD patients suffering from and/or diagnosed with NPH, regardless of whether they may be concurrently suffering from other conditions, such as AD.

The relationship between NPH and AD in the patient population treated by the methods of the present invention may be understood based on a hypothesis of the inventors herein. In particular, the inventors hypothesize that AD and NPH are on a continuum of diseases of CSF circulatory failure, and that an initially dominant physiologic change determines whether this failure manifests as AD or as NPH or a combination of the two. If the more marked physiologic change initially is a decline in CSF production—an "afferent" limb failure—then AD results. If instead an increase in the resistance to CSF absorption, ($R_{out}$) predominates—an "efferent" failure—NPH results. Once either disease manifests, the pathophysiologic changes which ensue may set the stage for the development of the alternate disease as well. The observed coincidence of AD and NPH may be the result of the mutual influence of these two clinical "phenotypes" of CSF circulatory failure. An AD-NPH confluence may result, with features of both diseases. The inventors propose a new nosologic entity of CSF circulatory failure, encompassing patients who have AD, NPH, or a combined AD-NPH pathology. The latter "hybrid" disease may comprise an important subset of patients with dementia. The present invention does not rely on the correctness of this hypothesis, but it is believed that the hypothesis is useful in explaining why the treatment will be effective for both NPH patients and patients suffering from both NPH and AD.

Methods according to the present invention for treating patients suffering from NPH comprise identifying a patient suffering from NPH, typically based on the symptoms of dementia, urinary incontinence, and apraxia of gait, although individual patients were usually not suffering from all three of these symptoms concurrently. Methods and protocols for diagnosing NPH in patients are described in Boon A W, Tans, J Th J, Delwel E J, Egler-Peerdeman S M, Hanlo P W, Wurzer A L, Avesaat C J J, de Jong D A, Gookens H J M, Hermans J. Does CSF outflow resistance predict the response to shunting in patients with normal pressure hydrocephalus? Acta Neurochir 1998; (suppl) 71:331–3.

After an NPH patient has been identified, the patient is treated to establish a controlled drainage pathway from a CSF space in order to remove CSF from the patient even when elevated pressures are not present. In a first particular protocol, the CSF will be drained at a substantially continuous flow rate for so long as pressure in the ventricle or lumbar subarachnoid space, a CSF space, remains within a normal range, typically from −170 mm $H_2O$ to 200 mm $H_2O$. CSF will be removed at a rate typically in the range from 0.01 ml/min to 0.2 ml/min, preferably from 0.03 ml/min to 0.1 ml/min, and often in the range from 0.04 ml/min to 0.06 ml/min. It will be appreciated that the CSF drainage will usually be stopped when the differential pressure (as defined hereinafter) falls to a preselected pressure below 75 mm $H_2O$, typically being stopped at 20 mm/$H_2O$ to prevent CSF overdrainage. CSF flow, however will not usually be stopped when the pressure exceeds 100 mm $H_2O$. Such elevated pressures will often be experienced by NPH patients, particular at night, and it will usually be beneficial to continue drainage of CSF when pressures are elevated above the 200 mm $H_2O$ level. In some instances, it will be desirable to increase the drainage rate when the pressure becomes elevated above the normal pressure range. While many prior art hydrocephalus shunts will also provide for drainage at such elevated pressure levels, it must be understood that such shunts do not provide for the continuous, controlled low-flow drainage at normal CSF pressures as is required by the methods of the present invention.

In the protocols of the present invention which provide substantially continuous flow at normal CSF pressures, it will frequently be desirable to maintain a relatively uniform flow rate as the CSF pressure varies over the nominal "normal" range. Typically, the CSF flow rate will vary by no more than ±75% as the CSF space pressure varies over said normal range, often varying by no more than ±50%, and sometimes varying by no more ±20%.

In preferred and exemplary methods of the first CSF drainage protocol, establishing the flow path will usually comprise implanting a conduit between a location in the CSF space, typically but not necessarily in a patient ventricle, and a drainage location outside of the CSF space, typically the peritoneum, the venous system, pleural space, the scalp, a gall bladder, or the like. The conduit will typically include a flow control component which is adapted to control the CSF drainage flow rate according to the parameters defined above.

In a second flow drainage protocol according to the present invention, the flow path will be modulated to provide for "volumetric removal" of CSF from the CSF space, as generally described in prior application Ser. No. 10/224,046, the full disclosure of which has been incorporated herein by reference. By "volumetric removal" it is meant that the methods of the present invention will remove a volume of CSF within a target range during a predetermined time period, usually one day (24 hours) rather than in response to elevated intracranial pressures. For the treatment of NPH, optionally in conjunction with AD, the volume of CSF removed during each one day time period will be in the range from 15 ml to 1500 ml, usually from 40 ml to 300 ml, and more usually from 60 ml to 100 ml. Changes in intracranial pressure resulting from patient posture, positions, or other factors, will have little or no effect on the volume of CSF to be removed.

While the preferred volumetric removal ranges for each one-day period have been set forth, it will be appreciated that these volumes could be removed on an hourly, weekly, or other periodic time basis. Moreover, while it will generally be preferred to remove the same volumetric amounts of CSF over successive one-day or other successive time periods, the present invention also encompasses methods and apparatus for removing different volumes of CSF over successive time periods and/or the removal of identical CSF volumes of different successive time periods. For example, it may be desirable to remove a majority or all of the daily CSF volume during the day when the patient is active, which can be accomplished with the present invention. Alternatively, it might be desirable to remove CSF at night while the patient sleeps, which can also be accomplished with the present invention.

Such volumetric removal may be accomplished in at least several ways. First, the volume of CSF drained over time may be measured and monitored. Once a target volume of CSF has been removed, an on-off or other control valve may be actuated to stop the flow. Such measurement and control may be performed once per day, or many times per day. In either case, however, the total volume of CSF removed in that day will fall within the above target ranges.

A second exemplary approach can employ a pump together with measurement, control, and monitoring of the amount of CSF removed. Starting and stopping of the CSF removal can be accomplished simply by turning off and on the pump. Optionally, valve(s) could also be provided for a more complete shut-off.

Third, the CSF could be removed using a positive displacement pump having a flow output controlled by pump speed, and not dependent on patient intracranial pressure. Thus, the target volume of CSF to be removed can be programmed by turning on and off the pump in a predetermined pattern. The pump could be turned on once per day to remove the total desired target volume, or could be actuated numerous times during the day to achieve the same volume.

A fourth approach could use one or more accumulators in combination with one or more on-off valves. By allowing the accumulator to fill and drain in a time-controlled manner, known volume(s) of CSF can be drained during each one-day period. The accumulator could have a blocking valve immediately upstream, in which case the valve would be opened in order to fill the accumulator and be closed after the accumulator is filled. Drainage of the accumulator could be controlled by a second valve. Alternatively, the accumulator could have a flow resistor at its outlet which would permit the accumulator to fill rapidly (the valve would provide a low resistance entrance) while a relatively low percentage of the volume is lost through the flow restrictor. After the valve is closed, the CSF could then drain to the disposal location. The volume of the accumulator and the outlet flow rate would, of course, have to be selected so that there would be sufficient time for drainage of the accumulator before the next cycle of operation was to be initiated.

The accumulator could also have a single one-off valve at its outlet. In that case, the inlet would have to have a relatively high flow resistance. Filling of the accumulator with outlet valve closed would occur over a relatively long period. Once filled, however, the accumulator could be rapidly emptied by opening the outlet valve which would have a very low flow resistance. While the outlet valve was open, flow through the high flow resistance inlet would be relatively low. After drainage, the outlet valve would be closed, allowing the accumulator to once again fill. The next cycle of drainage would then occur according to the predetermined pattern. In all cases, the accumulator will typically have a fill volume in the range from $10^{-3}$ ml to 40 ml, usually from 0.1 ml to 2 ml, and will be filled and drained from once to $1.5 \times 10^6$ times, usually from 6 to 15,000 times, during each one-day period.

Thus, volumetric methods according to the present invention for removing CSF from a patient's subarachnoid space (i.e., any CSF space below the arachnoid membrane) comprise establishing a flow path between the subarachnoid space and a drainage location in the patient's body. Flow through the flow path is then modulated to remove a target volume of CSF within each one-day period. The target volume of CSF to be removed is preferably in the ranges set forth above. Modulating the flow through the flow path may comprise opening an on-off valve. In such case, the desired volume of CSF to be removed may be controlled by measuring the time the valve has been opened and closing the valve after a predetermined period of time has elapsed. Alternatively, the desired CSF volume to be removed may be controlled by measuring the volume of CSF which has been removed over time and closing the valve after a predetermined volume of the fluid has been removed. In either case, the valve may be opened once and closed once during each one-day period, or may be opened and closed multiple times, where the aggregate or total volume removed as a result of each valve opening and closing results in the total removal within the above-described target volume range. When the valve is opened and closed based on time, the time duration will typically be in the range from 1 hour to 8 hours or the flow rate is in the range from 0.5 ml per hour to 40 ml per hour. In some instances, the valve will be opened many times, e.g., from 2 to $10^8$ times, usually from 20 to $10^5$ times, and more usually from 50 to 300 times, during each one-day period. Thus, the volume of CSF removed in any single valve opening may vary greatly, typically being from $10^{-5}$ ml to 40 ml, usually from 0.01 ml to 30 ml, and more usually from 0.1 ml to 19 ml, each time the valve is opened. It is also important to control the drainage rate of CSF so that it never exceeds a safe level; i.e., a level that will minimize the development of overdrainage complications such as slit ventricles, delayed proximal obstruction, subdural fluid collections, etc. Thus, the flow path will be arranged so that the CSF removed in any 15-minute period will not exceed 15 ml and in any one hour, will not exceed 50 ml.

DETAILED DESCRIPTION OF THE INVENTION

Figure 1:
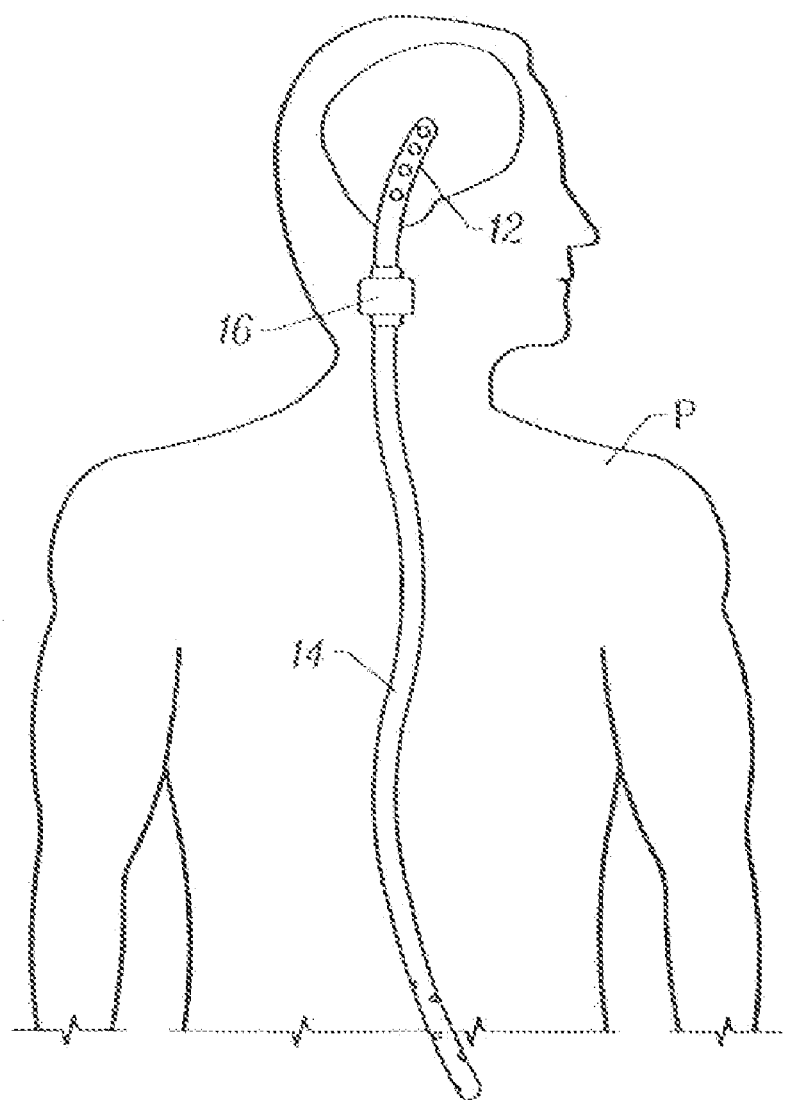
FIG. 1 is a schematic illustration showing the components and placement of a conventional system for removing CSF from a CSF space of the brain.
Figure 1A:
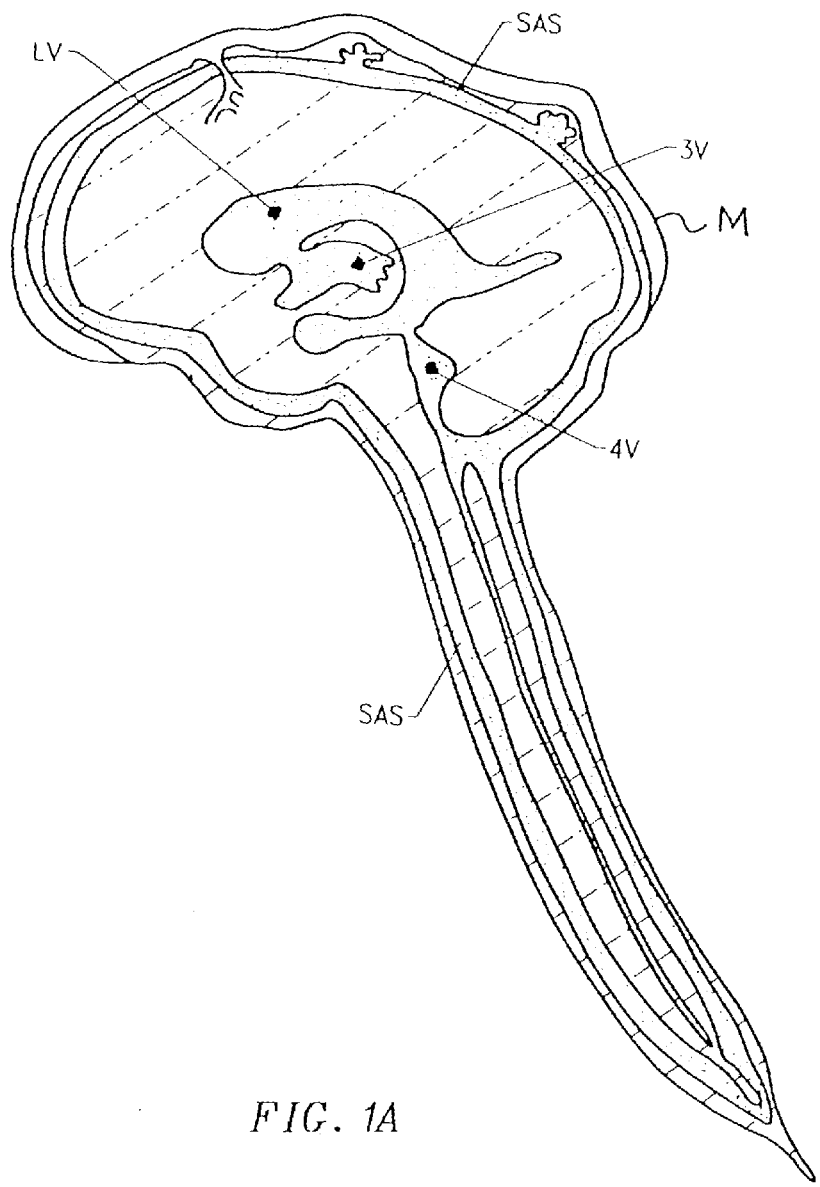
FIG. 1A is a more detailed view of the CSF space including the brain and the spinal column.

The brain and spinal cord are bathed in cerebrospinal fluid (CSF) and encased within the cranium and vertebral column inside a thin membrane known as the meninges (FIG. 1A). The space within the meninges M, which is the three-membrane complex enveloping the brain and spinal cord, consists of the subarachnoid space SAS, including the ventricles (including the lateral ventricle LV, third ventricle 3V, and fourth ventricle 4V), the vertebral column, and the brain interstitial spaces. The total space within the meninges M including the CSF contained in the brain's natural cavities is referred to herein as the "CSF space." The volume of the brain intracranial spaces is on average about 1700 ml. The volume of the brain is approximately 1400 ml, and the volume of the intracranial blood is approximately 150 ml. The remaining 150 ml is filled with CSF (this volume will typically vary within 60 ml to 290 ml). The CSF circulates within the CSF space. CSF is formed principally by the choroid plexuses in the lateral, third and fourth ventricles, which secrete about 80% of the total volume of the CSF. Other CSF sources producing the remainder are the vasculature of the subependymal regions, and the pia matter. The total volume of the CSF is renewed several times per day, so that about 500 ml are produced every 24 hours (equivalent to about 20 ml/hr or 0.35 ml/min) in healthy adults. The production rate is lower in the old and the very young.

The cerebrospinal fluid is absorbed primarily through the arachnoid villi, located principally over the superior surfaces of the cerebral hemispheres. Some villi also exist at the base of the brain and along the roots of the spinal nerves. The absorptive processes include bulk transport of large molecules as well as diffusion across porous membranes of small molecules. The production and absorption of CSF are well described in the medical literature. See, e.g., Adams et al. (1989) "Principles of Neurology," pp. 501 502.

While CSF is naturally absorbed and removed from circulation, as just described, it is presently believed normal pressure hydrocephalus, a common form of adult-onset, chronic hydrocephalus, appears to result from an increase in CSF outflow resistance, perhaps at the arachnoid villi. Such increased outflow resistance can lead to elevated CSF pressure and ventriculomegaly. While the pathognomonic abnormality in NPH is compression of the extracellular compartment and increased outflow resistance, it appears that CSF production is also impaired. CSF production in patients with NPH is significantly decreased compared to CSF production measured in acute hydrocephalus patients or those with Parkinson's disease. Such decrease is similar to that observed among Alzheimer's patients. Although in animal models there is no evidence for physiologic "down-regulation" of CSF production as a response to acute hydrocephalus, in chronic hydrocephalus down-regulation of CSF production has been demonstrated, but the model has been criticized as unlike human chronic hydrocephalus. Such a regulatory response might play a role in decreased CSF production in NPH. Hydrocephalus-induced pathologic changes in choroid plexus also could be a factor: among individuals with a history of hydrocephalus, both stromal sclerosis and epithelial atrophy of the choroid have been described. Such changes could lead to a reduced CSF secretory capacity. As a consequence of relatively decreased CSF turnover, clearance of macromolecules would be expected to be diminished, as is observed in AD. Based on such observations, Applicants believe that NPH may result at least partly from the inability of a patient to clear toxins from the CSF. Thus, methods which improve CSF turnover and clearance of toxic substances would be expected to improve the symptoms of NPH, particularly the dementia observed in NPH.

The removal of CSF for the treatment of NPH according to the methods of the present invention can be accomplished using a wide variety of apparatus which are capable of collecting CSF in the CSF space, preferably from the intracranial ventricles, but also in other regions such as the lumbar thecal space, and transporting the collected fluid to a location outside of the CSF space. Usually, the drainage location will be an internal body location, such as the venous system or the peritoneal cavity, which is usually capable of harmlessly receiving the fluid and any toxic substances, but it is also possible to externally dispose of the CSF using a transcutaneous device. An exemplary system for removing CSF from a patient's CSF space is illustrated in FIG. 1 and includes an access component 12, a disposal component 14, and a flow control component 16.

Figure 3:
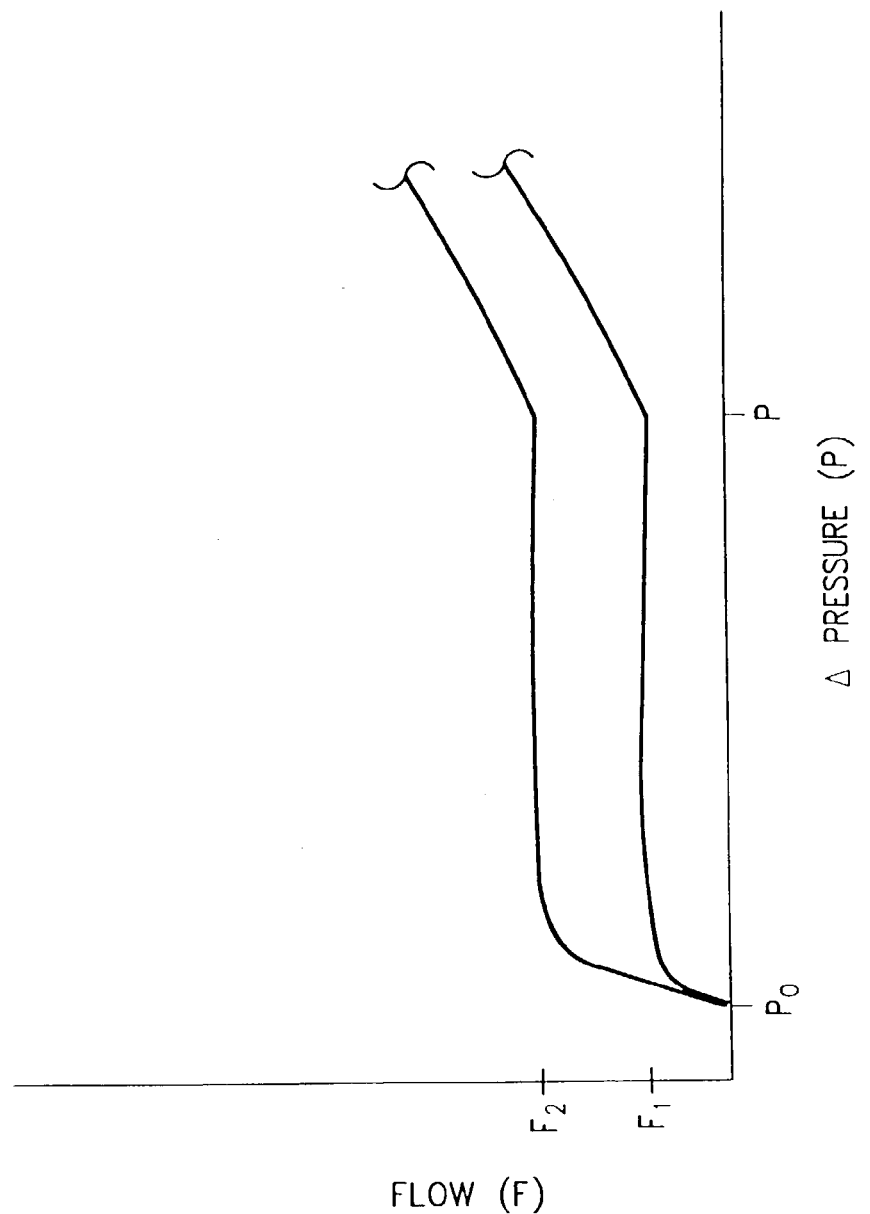
FIG. 3 illustrates exemplary flow-pressure relationships for the devices and methods of the present invention.

While the system of FIG. 1 in general will be similar to those used for the treatment of high pressure conditions, specific characteristics of the flow control component will be quite different to achieve CSF removal at normal pressure range as required by the methods of the present invention. Referring to FIG. 3, the devices and methods of present inventions are particularly intended to maintain a relatively constant flow rate of CSF from the CSF space at normal intracranial pressures P (e.g. −170 mm $H_2O$ to 200 mm $H_2O$ relative to ambient). For safety, the devices and methods will be configured to remove little or no CSF at intracranial pressures below a threshold value $P_0$ which is at or near the lowest expected intracranial pressure for an upright patient, typically −170 mm of $H_2O$. At intracranial pressures above $P_0$, the CSF flow rate F will usually be between a lower values $F_1$ and an upper value $F_2$, with particular ranges set forth above. Usually, the flow rate F will be at a relatively constant level, with the rate preferably being pressurecorrected so that it does not vary by more than ±75%, preferably by no more than ±50%, and more preferably by no more than ±20% for intracranial pressures within the expected ranges. As observed in FIG. 3, it is desirable that the flow rate F be relatively constant at least over the range $P_0$ to $P_1$, and more preferable that the flow rate remains constant for even higher differential pressures since the present invention is not intended to treat excessive intracranial pressure, but rather to remove the CSF at a relatively low, constant rate regardless of the differential pressure (so long as P is above the threshold $P_0$).

Figure 4:
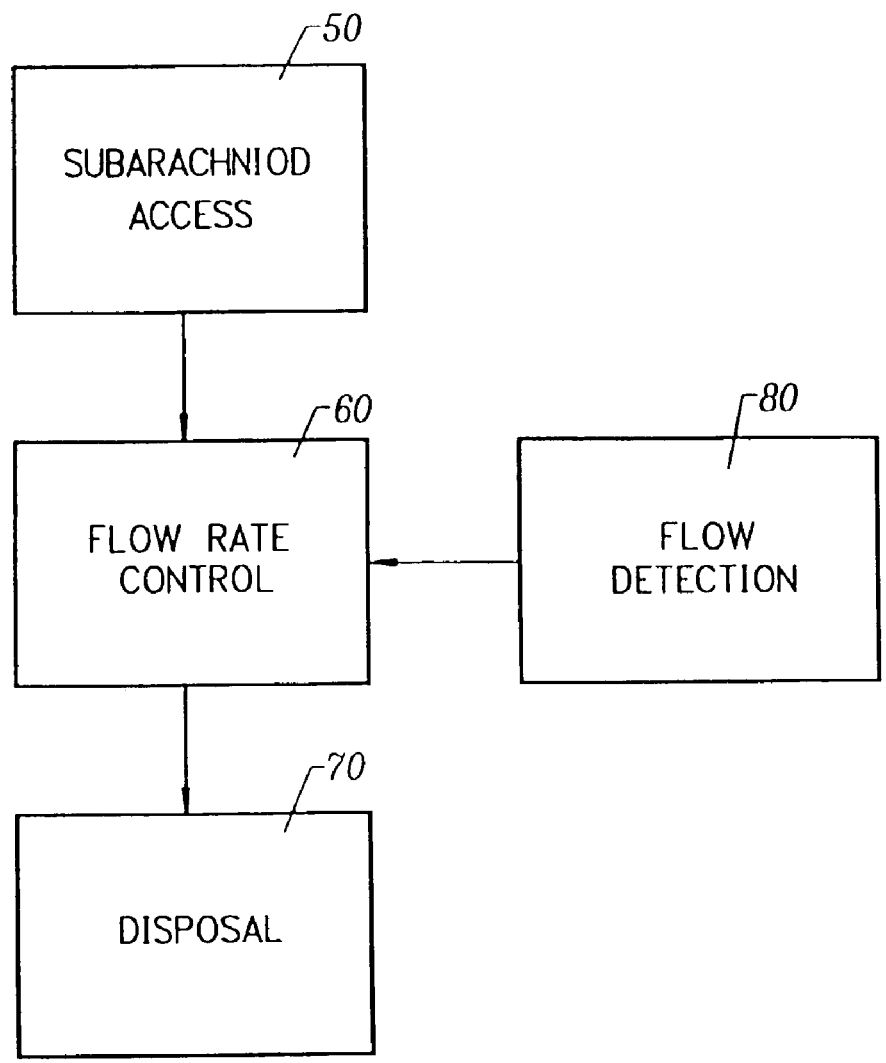
FIG. 4 is a schematic illustration of apparatus according to the present invention for draining CSF from a CSF space of the patient's brain in accordance with the principles of the present invention.

Apparatus according to the present invention for removing CSF from a CSF space is illustrated schematically in FIG. 4. Apparatus will generally include an access component 50, a flow rate control component 60, optionally a disposal component 70, and optionally a flow or detection component 80. With the exception of the flow rate control component 60, present invention may use components of a type described in U.S. Pat. No. 6,264,625, the full disclosure of which is incorporated herein by reference. The flow rate control component 60, however, will be constructed specifically to achieve the flow-pressure response characteristics which have been discussed previously.

Figure 2:
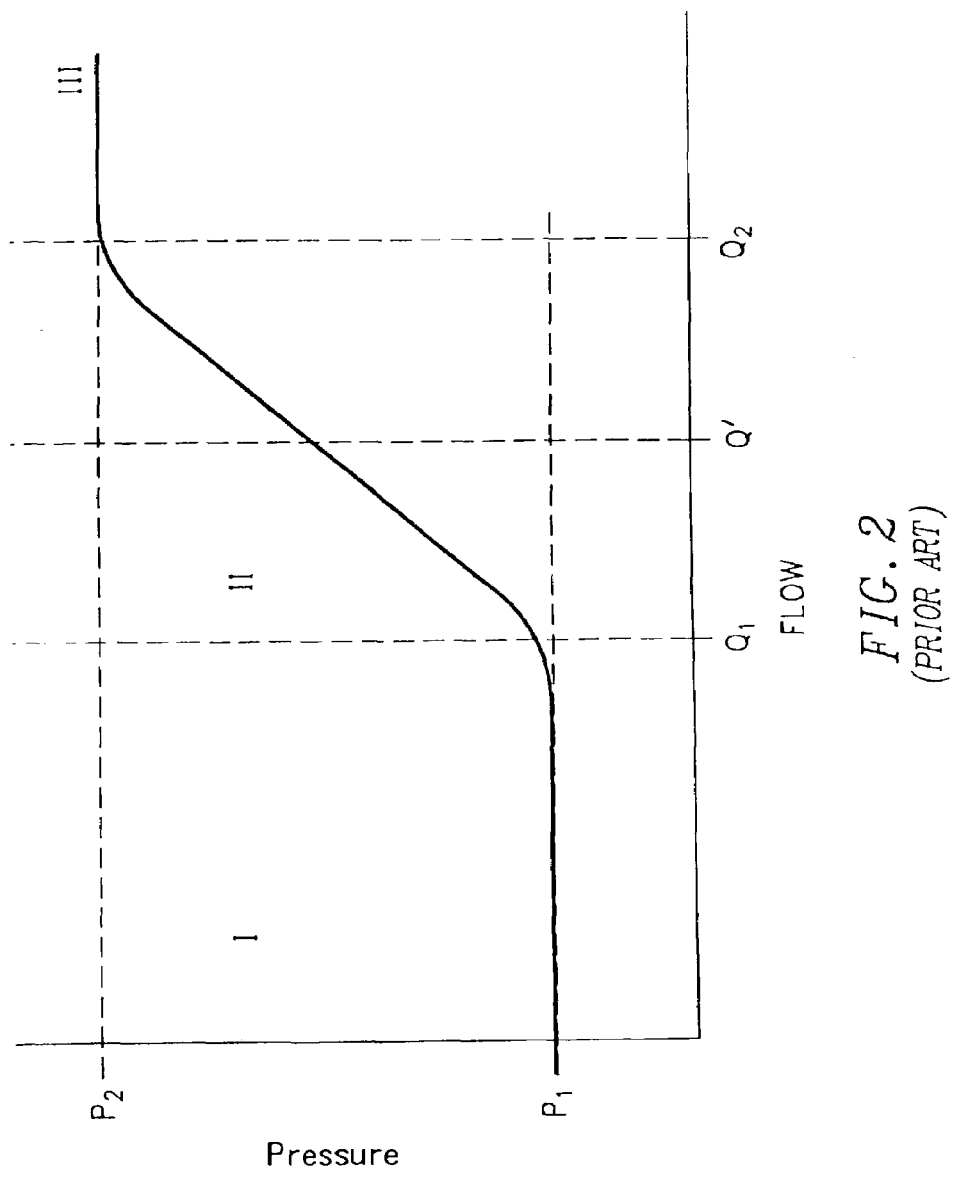
FIG. 2 illustrates the pressure-flow relationship of a conventional flow valve used in system such as those shown in FIG. 1 for treating high-pressure hydrocephalus, wherein "$Q_1$, Q" and $Q_2$ represent increasing flowrates through the valve.
Figure 5A:
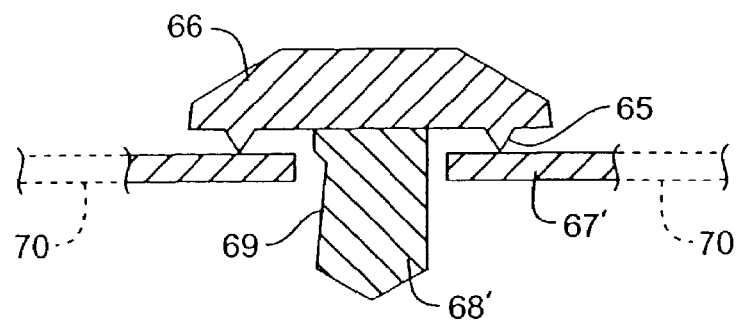
FIGS. 5A–5C illustrates modifications that can be made to the flow control valve of U.S. Pat. No. 4,781,672, so that the valve described in that patent will display flow-pressure characteristics in accordance with the principles of the present invention.
Figure 5B:
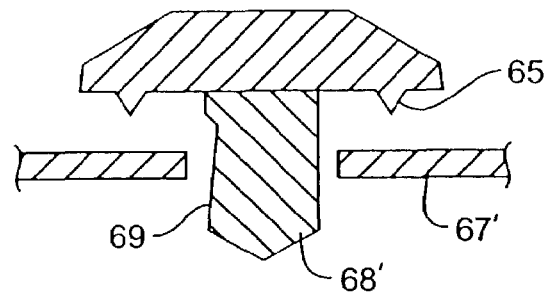
Figure 5C:
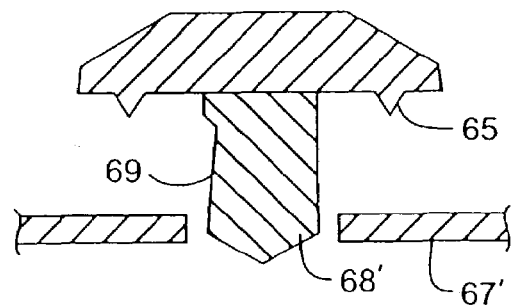

As illustrated in FIGS. 5A–5C, a passive flow control valve of the type illustrated in U.S. Pat. No. 4,781,672, may be modified to provide the flow-pressure characteristics of the present invention. The full disclosure of U.S. Pat. No. 4,781,672, is incorporated herein by reference, and the flow/pressure characteristics of this valve are shown in FIG. 2. By modifying the characteristics of valve seat 67 and valve stem 68 (and optionally the diaphragm and/or other valve components) in that patent, the flow characteristic of the present invention may be achieved. In particular, by substituting valve seat 67' and valve stem 68', as illustrated in FIGS. 5A–5C the desired flow characteristics can be achieved. The valve seat 67' and valve stem 68' comprise an orifice and contoured valve plug according to the claims in the present application. A notched, sliced or tapered surface 69 maybe formed on one side of the valve plug 68' to change the available annular area between the plug and the seat 67' as the plug is raised relative to the seat, as shown in FIGS. 5B and 5C. When the valve structure is closed, as shown in FIG. 5A, an annular ring 65 formed on the lower surface of a stationary component 66 seats against an upper surface of the valve seat 67'. Thus, the valve is closed. As CSF flows into the valve structure, it exerts pressure against the diaphragm 70 and valve seat 67', which is mounted in a diaphragm 70 (shown in broken line in FIG. 5A) causing the valve seat to move lower as shown in both FIGS. 5B and 5C. With a relatively low differential pressure, the valve seat 67' lowers partly down the valve plug 68', entering into or further a portion of the notched region 69 which decreases the annular space between the plug 68' and the valve seat 67'. As the inlet pressure further increases (and thus the differential pressure also increases), the valve seat 67' moves further down, moving to a portion of the notch where the available flow area through the valve seat 67' is reduced. Thus, the valve structure is pressure-compensated so that the resistance to flow increases as the differential pressure increases, which acts to maintain a constant flow rate regardless of the system differential pressure. The total travel of the valve from FIGS. 5A–5C will generally be selected to occur so that the valve first opens at a differential pressure of approximately $P_0$ and fully opens at a differential pressure which is well above the maximum expected differential pressure P, so that relatively constant flow rates may be maintained over the entire expected differential pressure range $P_0$ to $P_1$ (FIG. 3). In all cases, the values P, of differential pressure, are the sum of the intracranial pressure, hydrostatic pressure, and pressure at the release site, e.g intra-abdominal pressure.

Figure 6A:
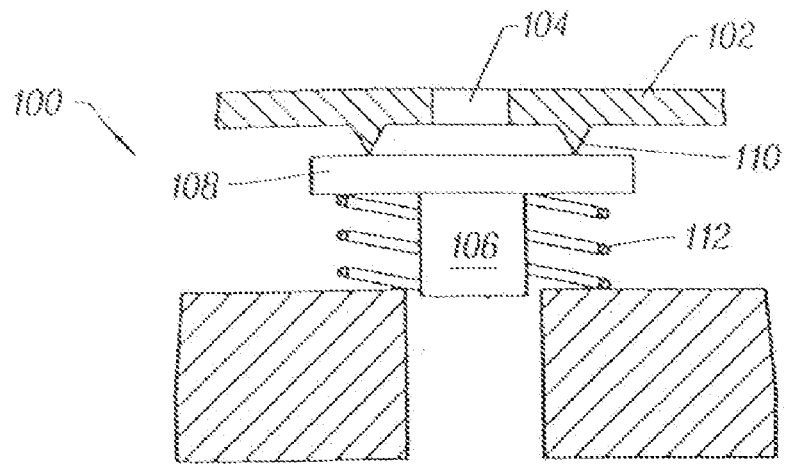
FIGS. 6A and 6B illustrate an alternative embodiment of a valve mechanism for practicing the present invention.
Figure 6B:
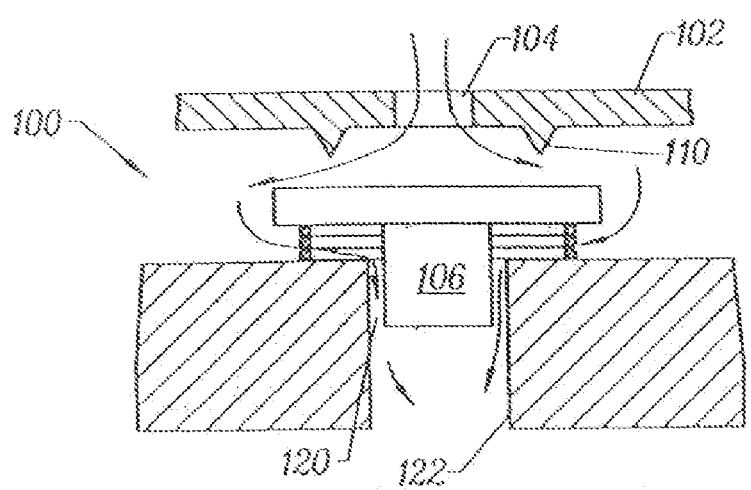

While modification of the commercially available Orbis-Sigma® or OSV II valve units will be particularly convenient, a wide variety of other specific valve designs will also be available to provide the desired pressure-flow characteristics of the present invention. Referring now two FIGS. 6A and 6B, a valve structure 100 comprises a plate 102 having an inlet orifice 104. A reciprocating valve plug 106 is attached to the plate 108 on its upper end. The plate seats against a sealing ring 110 projecting downwardly from the plate 102 so that the valve is closed until a sufficient CSF inlet pressure develops across orifice 104 to open valve plug 106 against a spring 112 which is under slight compression. Once the valve is opened, as shown in FIG. 6B, CSF will flow past the plate 108 and into the annular space 120 between the plug 106 and a cylindrical wall 122 formed in the valve body. As the inlet pressure and the differential pressure increase, the plug 120 will be further lowered, thus increasing the length of the annular lumen which is formed between the plug 106 and the cylindrical wall 122. As the lumen length further increases, the resistance to flow also increases, thus making the valve structure 100 a pressure-compensating structure in accordance with the principles of the present invention. That is, as the differential pressure across the plug 106 increases, the plug will be displaced further into the cylindrical space 122. A force balance will be reached when the upward force of spring 112 becomes equal the downward force on the plug 106 by the differential pressure across the plug. The valve plug will thus move downward to increase flow resistance in response to increased differential pressures.

Figure 7:
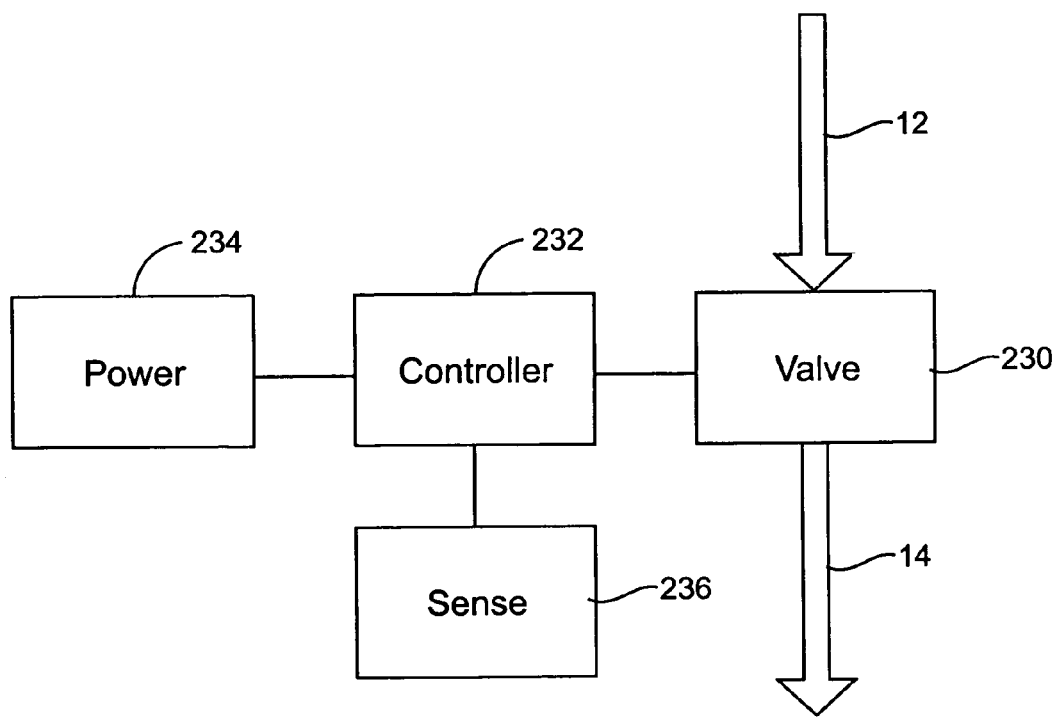
FIG. 7 is a block diagram illustrating a controlled valve system for volumetric CSF removal according to the methods of the present invention.

In addition to employing the pressure-responsive flow control modules as described, the methods of the present invention may rely on the volumetric removal of CSF as illustrated in FIGS. 7 through 11/AB. Referring now to FIG. 7, a first control system and protocol for performing the methods of the present invention will be described. An on-off or other flow control valve 230 is provided between a ventricular catheter 12 and a peritoneal catheter 14, which may be essentially identical to those described in connection with FIG. 1 above. The valve 230 will be turned on and off or modulated by a controller or actuator 232 which will have a power source 234. The power source may comprise a mechanical energy source, such as a spring, bellows, or the like, or more likely will comprise an electrical energy storage device, typically a chemical battery. In the latter case, the electrical energy storage device will preferably be rechargeable using external RF energy, optical energy, or the like. In the case of mechanical power sources, they may be recharged by patient motion, or the like.

The controller 232 is meant to be any instrument which utilizes power from source 234 to turn on and off or otherwise modulate the valve 230. The controller may further comprise control circuiting, timing circuitry, sensing circuitry, and the like to permit programmed or otherwise controlled operation of the valve 230. For the most part, it will be desirable to turn the valve on and off to permit a controlled volumetric drainage of the CSF. Such valve operation may be in response to a predetermined time schedule but will more effectively be in response to the measured drainage of the CSF during any period the valve is open.

When CSF drainage is being controlled based on volume, it will be necessary to sense the volume of flow using a sensing device 236. The sensing device will preferably totalize flow through the valve, and the controller 232 will turn on and off or otherwise modulate the valve flow periodically based on the total volumetric flow observed over time. Most simply, the valve could be opened once a day (based on a timer present in the controller 232 or sensor 236) and then closed after the sensor 236 has determined that the target volume has been drained. Such an approach would be effective so long as the maximum 15-minute and hourly depletion volumes described above are not exceeded. In other cases, it might be desirable to open and close the valve more than once during each one-day period, possibly opening and closing the valve up to $2 \times 10^8$ times as described above, or usually, the valve would be opened $10^5$ times or fewer, usually 300 times or fewer, and preferably 50 times or fewer.

When electrically powered controllers and sensors are employed, the valve will also typically be electrically controlled. Suitable electrically controlled valves are well described in patent and technical literature. Alternatively, mechanically controlled valves are described in U.S. Pat. No. 6,264,625, the full disclosure of which has previously been incorporated herein by reference.

Figure 8:
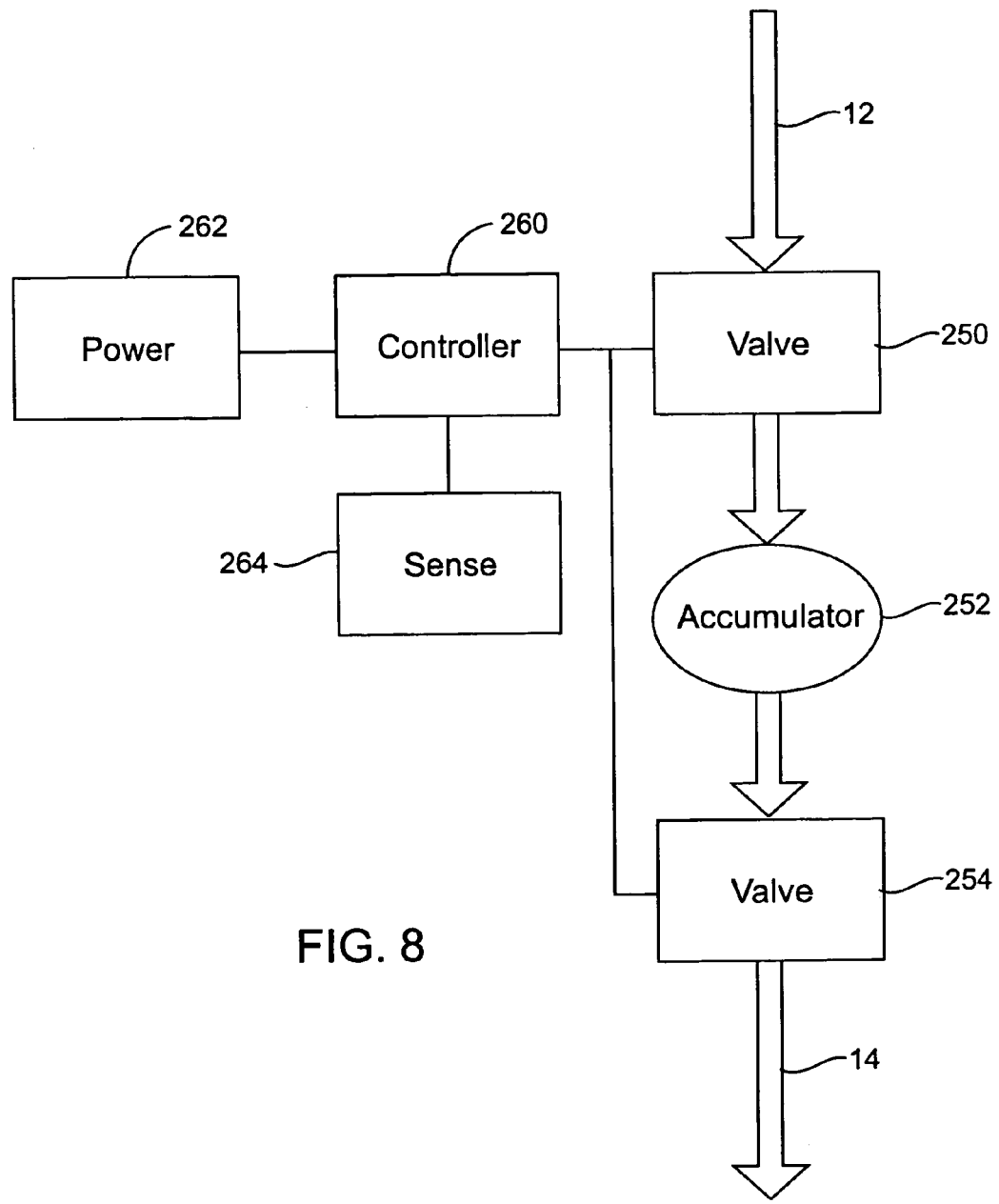
FIG. 8 is a block diagram illustrating an accumulator system suitable for volumetric CSF removal according to the principles of the present invention.

A CSF drainage system using an accumulator to measure the volumetric drainage is schematically illustrated in FIG. 8. The system of FIG. 8 will include at least one valve 250, an accumulator 252, and optionally a second valve 254 which may further optionally be used in place of the first valve 250, as described in more detail below. The system of FIG. 8 will also include a controller 260 for operating the valve 250 (and alternatively or additionally the valve 254), a power source 262, and optionally a sensor 264.

Figure 9:
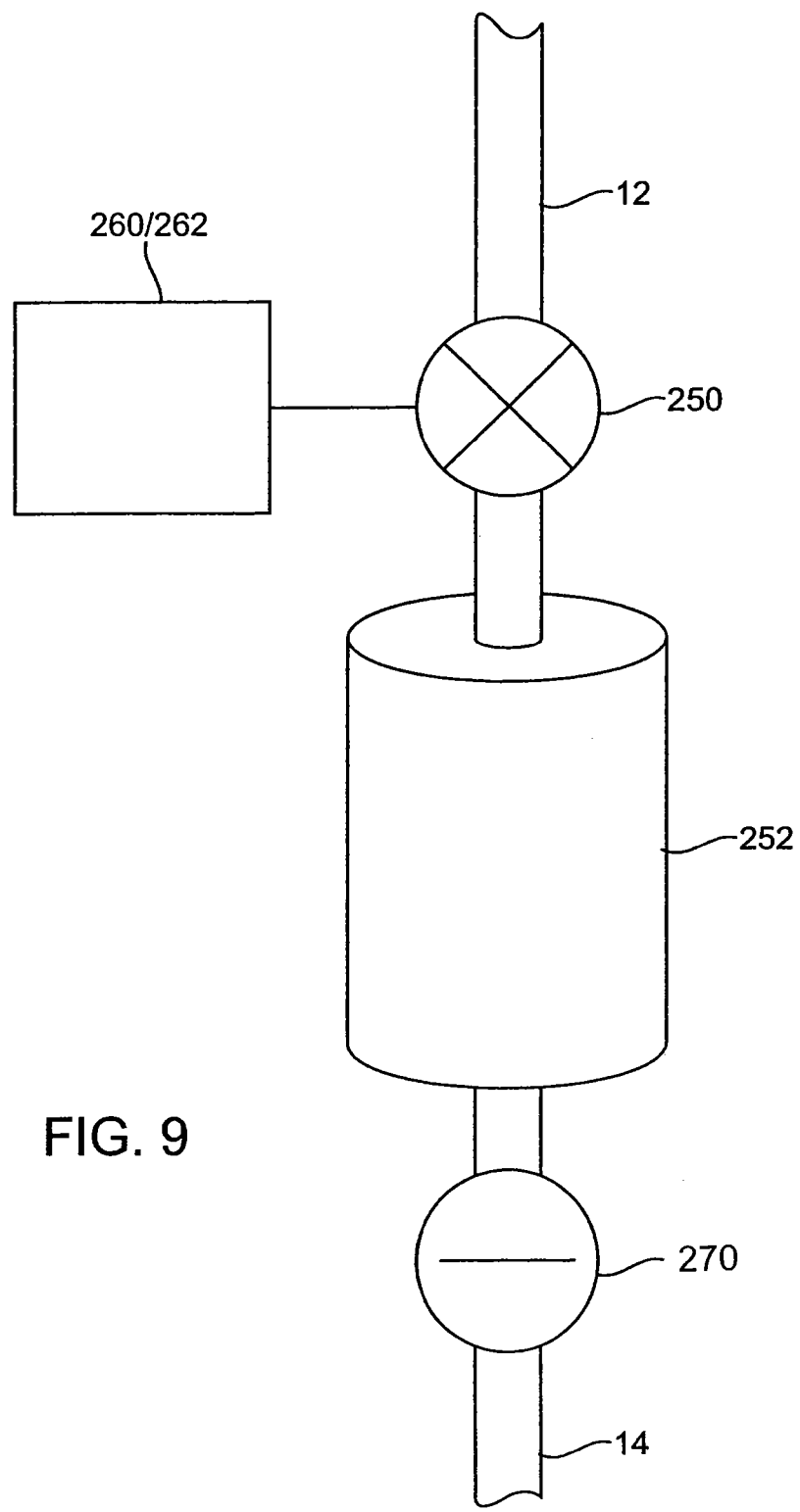
FIG. 9 is a schematic illustration of a first embodiment of an accumulator system having a controlled outlet valve.

A first example of a system employing an accumulator 252 is shown in FIG. 9. Ventricular cather 12 is connected to an on-off control valve 250 which is connected to a combined power supply and controller 260/262. The accumulator has a volume in the ranges set forth above, and is attached to the peritoneal catheter 14 through a flow restrictor 270. The flow restrictor 270 provides a flow resistance which greatly inhibits the out flow of CSF from the accumulator while the inlet valve 250 is open. Thus, the accumulator can be filled by opening valve 250 based on a signal from the controller/power supply 260/262. The signal can be provided based on a timer included within the controller 260, e.g., once per one-day period. The valve 250 will remain open for a time which is more sufficient to fill the accumulator 252. It will be appreciated that, once the accumulator 252 is filled. flow into the accumulator will essentially stop, although a small amount of leakage will, continue through the flow restrictor 270. After sufficient time has passed for the accumulator to be filled, the valve 250 will be closed, and the accumulator 252 allowed to drain over time through the flow restrictor 270. The cycle can then begin again, typically 24 hours or other fixed time interval later, after the accumulator 252 has completely drained. In this way, a very precise volume of CSF can be drained each one-day period. Of course, it would be possible to actuate valve 250 to perform two, three, four, or more cycles in any one-day period.

Figure 10:
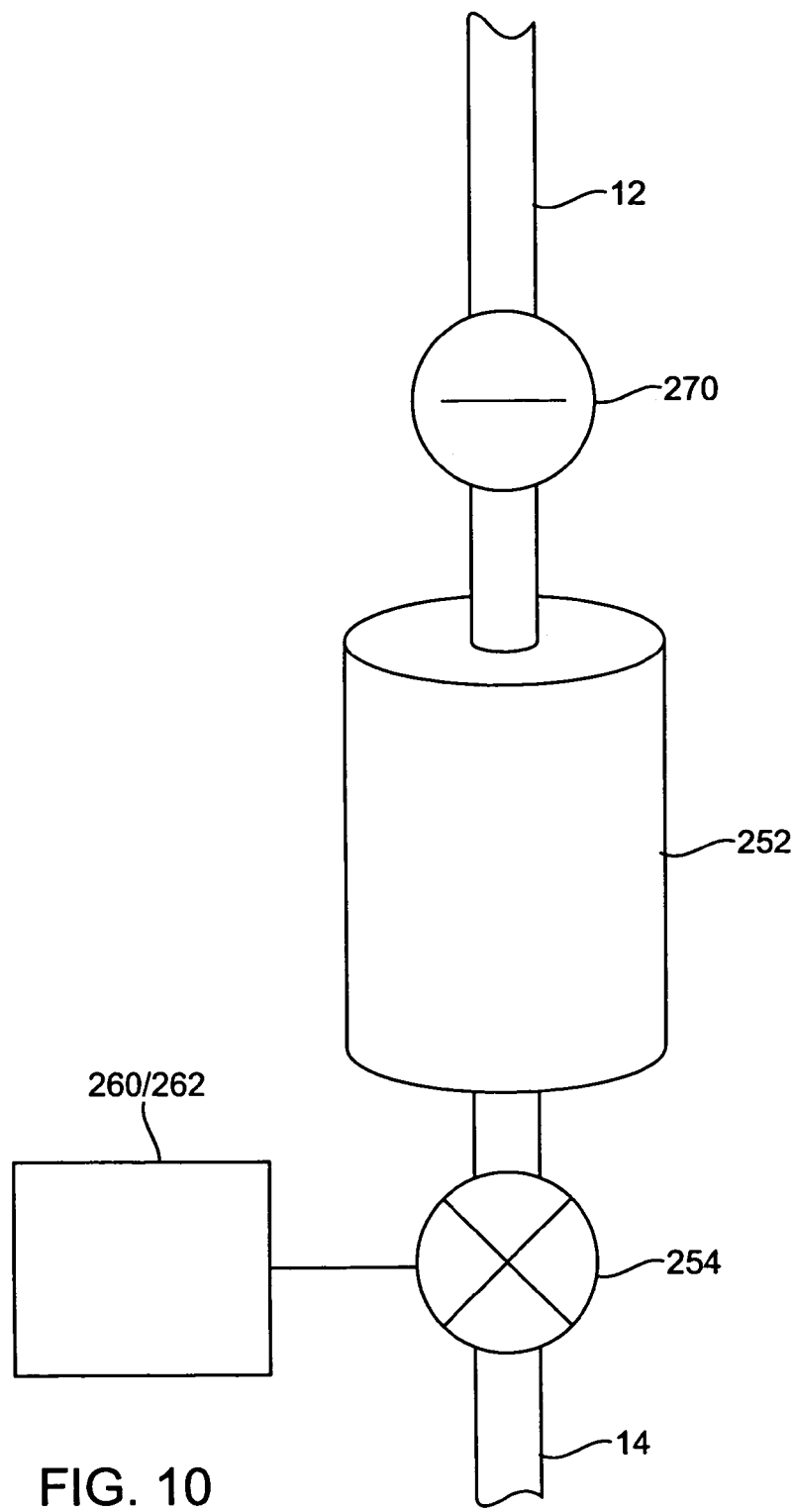
FIG. 10 is a schematic illustration of a second embodiment of an accumulator system having a controlled outlet valve.

A second specific example of the accumulator system of FIG. 8 is illustrated in FIG. 10. In the system of FIG. 10, the controller/power supply 260/262 is connected to drive the second on-off valve 254. The accumulator 252 fills from ventricular catheter 12 through the flow restrictive element 270. While the valve 254 is closed, the accumulator will slowly fill with flow essentially stopping after the accumulator has completely filled. After the accumulator is filled, the controller/power supply 260/262 can open the valve 254 which will permit rapid drainage of the accumulator 252. Of course, a small amount of CSF will drain through the flow restrictor 270, but such leakage will be very small when compared to the volume of CSF released from the accumulator 252. After sufficient time has passed to permit complete emptying of the accumulator, the valve 254 will be closed, and filling of the accumulator will begin again. Such cycles of filling and draining can be performed once each one-day period, or multiple times depending on the precise target volume, volume of the accumulator, and the like.

The system of FIG. 8 can of course accomplish even more accurate measurement of the drained CSF using a pair of valves as illustrated in FIG. 8. In such case, the accumulator may be filled by opening valve 250 while valve 254 remains closed. The accumulator will fill entirely and may be left filled until it is desired to drain the accumulator. At that time, the valve 250 should be closed, and valve 254 opened to permit a rapid draining of the accumulator. After a sufficient time has been allowed for permitting drainage, or drainage of the accumulator is confirmed using the sensor 264, the valve 254 may be closed and valve 250 reopened to permit filling of the accumulator. As the filling and drainage of the accumulator 252 are precisely controlled by the valves 250 and 254, there will be no leakage as with the embodiments of FIGS. 9 and 10. The system of FIG. 8 will, however, will require greater power consumption to operate two valves.

Figure 11A:
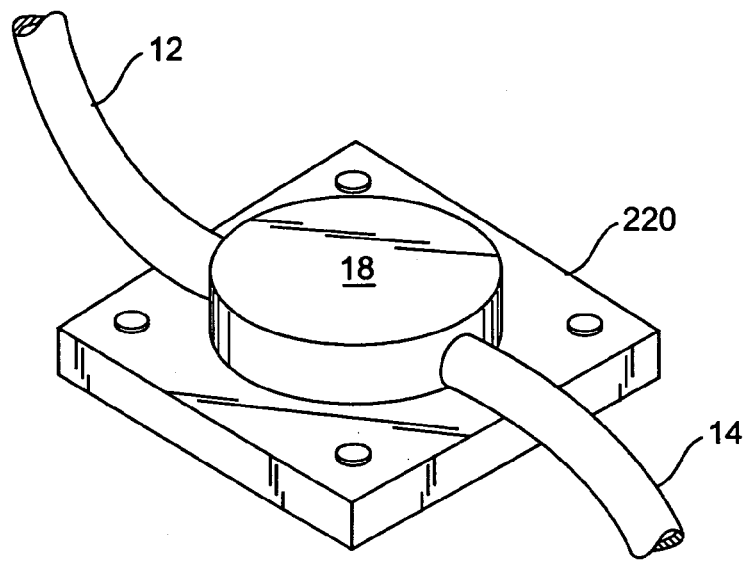
FIG. 11A shows a pump which may be used as the flow rate control device in the present invention.
Figure 11B:
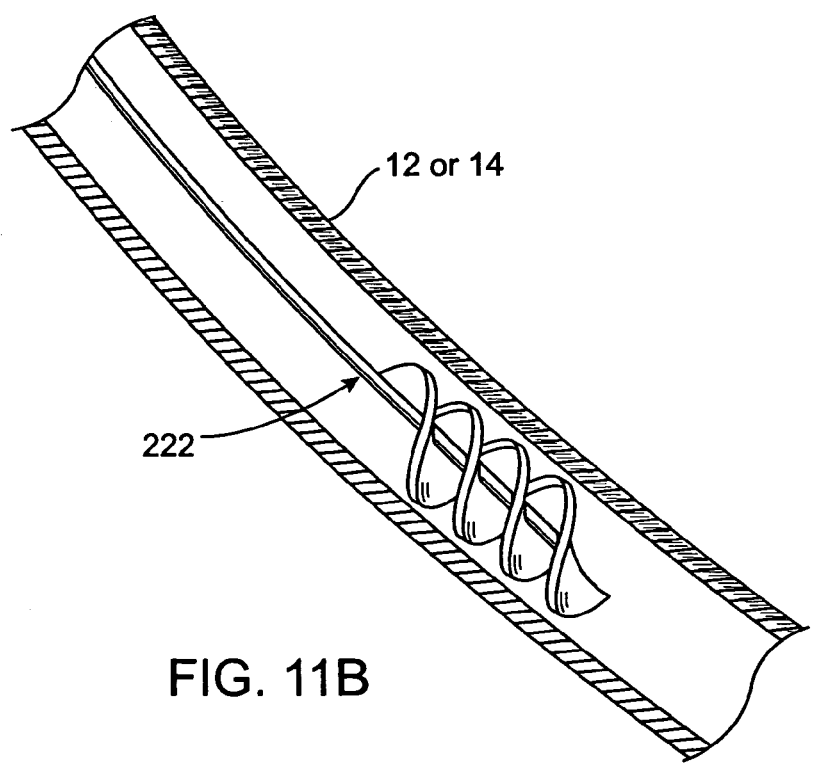
FIG. 11B shows a screw pump which may be used as the flow rate control device of the present invention.
Figure 12:
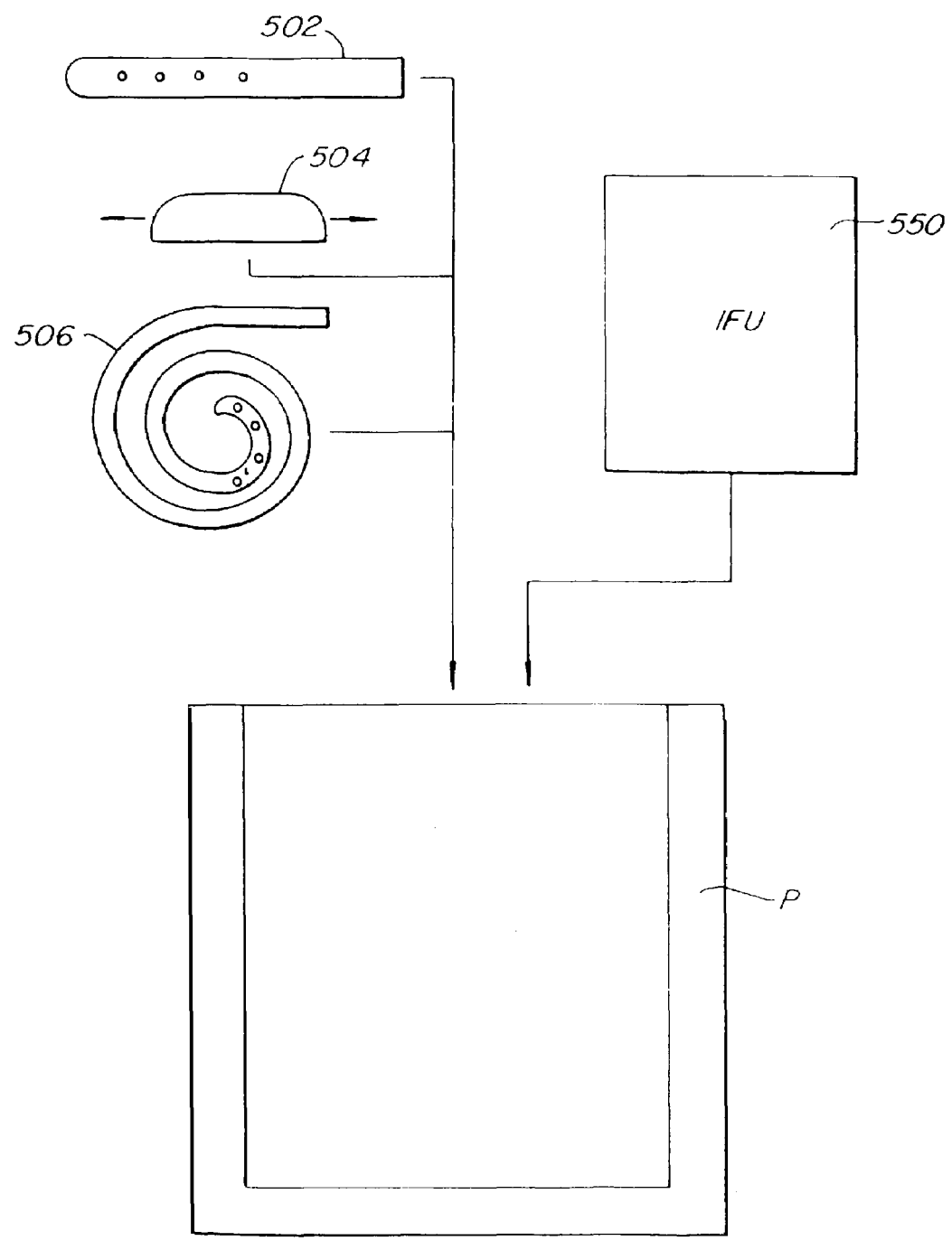
FIG. 12 illustrates a kit according by the present invention.

FIG. 11A shows an embodiment in which the fluid flow rate control device is an implantable pump 18 attached between venticular catheter 12 and peritoneal catheter 14. Pump 18 may be diaphragm pump, piston pump, rotor pump, peristalic pump, screw pump, or any other suitable pump. The power source for pump 18 may be a battery or other energy storage device, such as a mechanical flywheel with self-winding operation. The pump also may be remotely operated as is known in the art. Pump 18 further may be operated continuously or periodically, either on demand or according to a schedule or program. Pump 18 may be mounted on a baseplate 220 which is adapted for attachment to a port of the patient's anatomy. FIG. 11B illustrates a conventional screw pump arrangement where a screw shaft 222 is mounted for rotation within the ventricular catheter 12 and/or peritoneal catheter 14. The drive may he position in a hermetically sealed package mounted to toe conduit exterior and arranged within the thorax or peritoneum. The drive may he coupled to screw shaft 222 with a gear transmission as would he apparent to one of ordinary skill in the art. Other screw pump configurations also can he used such as those disclosed in U.S. Pat. No. 4,857,046 to Stevens et al. and U.S. Pat. No. 5,372,573 to Habib.

Such positive displacement pumps will drain a known volume of CSF based on each revolution, cycle, or the like. Thus, the total drained volume in any one-day period can be provided by operating the pump for a predetermined time at a predetermined rate. It is unnecessary to measure the flow or use an accumulator, although measured confirmation of flow might be valuable. It would also be possible to turn the pump off and on or otherwise control the volume delivered based on the measured flow using conventional feedback control algorithms implemented by the controller.

Systems according to the present invention may be provided in a kit form, as illustrated in FIG. 11. The kit will include the system components, such as ventricular access catheter 502, a flow control module 504, and a peritoneal catheter 506, together with instructions for use 550. The instructions for use 550 may set forth any of the methods described in the present application, including methods for implanting the system components within a patient so that the ventricular catheter is at the subarachnoid space, the flow control module is within the thoracic cavity, and the peritoneal catheter terminates within the peritoneum.

The system components and instructions for use will be provided within a package P, which may be in the form of a pouch, box, tray, tube, or other conventional medical package. The instructions for use 550 may be packaged within the package or may be printed on the package, or both. Usually, the system components, excluding instructions, will be sterilized within the package so they may be used without further sterilization.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for treating patients suffering from normal pressure hydrocephalus (NPH), said method comprising:
   identifying a patient suffering from NPH; and
   establishing a drain path from a cerebrospinal fluid (CSF) space of the patient, wherein the drain path will (a) drain CSF at a substantially continuous flow rate so long as pressure in the CSF space remains within a normal range, and/or (b) drain a target volume of CSF while pressure in the CSF space remains within the normal range; and
   wherein the drain path provides substantially continuous flow, at a rate in the range from 0.01 ml/minute to 0.2 ml/minute while pressure in the CSF space varies from −170 mm $H_2O$ to 200 mm $H_2O$.

2. A method as in claim 1, wherein identifying the patient comprising diagnosing symptoms selected form the group consisting of dementia, incontinence, and apraxia of gait.

3. A method as in claim 1, wherein the patient further suffers from Alzheimer's disease (AD).

4. A method as in claim 1, wherein the patient does not suffer from Alzheimer's disease (AD).

5. A method as claim 1, wherein the drain path extends into a peritoneal space, a pleural space, the venous system, a scalp, a gall bladder, or an external space.

6. A method in claim 1, wherein the drain path will remove CSF at a rate in the range from 0.01 ml/minute to 0.1 ml/minute over said pressure range.

7. A method as in claim 6, wherein the drain path will remove CSF at a rate in the range from 0.04 ml/minute to 0.06 ml/minute over said pressure range.

8. A method as in claim 1, wherein the CSF flow rate varies by no more than ±75% as the CSF space pressure varies over said range.

9. A method as in claim 8, wherein the CSF flow rate varies by no more than ±50% as the CSF space pressure varies over said rage.

10. A method as in claim 9, wherein the CSF flow rate varies by no more than ±20% as the CSF space pressure varies over said range.

11. A method as in claim 1, wherein the drain path will stop the flow of CSF from the subarachnoid region when differential pressure falls to a preselected pressure below 75 mm $H_2O$.

12. A method as in claim 1, wherein establishing comprises implanting a conduit between the CSF space to a drainage location, wherein said conduit comprises a flow control component adapted to control the CSF flow rate in the range from 0.01 m/minute to 0.2 ml/minute while pressure in the CSF space varies from −170 mm $H_2O$ to 200 mm $H_2O$.

13. A method as in claim 12, wherein the flow control component is adapted us control the CSF flow at a rate in the range of 0.03 ml/minute to 0.1 ml/minute over said pressure range.

14. A method as in claim 13, wherein the flow control component is adapted to control the CSF flow from 0.04 ml/minute to 0.06 ml/minute over said pressure range.

15. A method as in claim 12, wherein the flow control component establishes CSF flow which varies no more than ±75% in response to a CSF space pressure which varies over said range.

16. A method as in claim 15, wherein the flow control component establishes a CSF flow rate which varies no more than ±50% in response to a CSF space pressure which varies over said range.

17. A method as in claim 16, wherein the flow control component establishes a CSF flow rate which varies by no more ±20% in response to a CSF space pressure which varies over said range.

18. A method as in claim 12, further comprising stopping the flow of CSF from the CSF space when differential pressure falls below 75 mm $H_2O$.

19. A method as in claim 1, wherein flow path modules flow through a flow path to remove the target volume of CSF within a predetermined time period.

20. A method as in claim 19, wherein the predetermined time period is one day.

21. A method as in claim 20, wherein the target volume is the same for each one-day time period.

22. A method as in claim 19, wherein the flow path removes different target volumes of CSF in at least some successive predetermined time periods.

23. A method as in claim 19, wherein the flow path removes target volumes of CSF in predetermined time periods having different lenghts.

24. A method as in claim 21, wherein the target volume of CSF to be removes in the one-day period is in the range from 15 ml to 1500 ml.

25. A method as in claim 19, wherein the flow path modulates flow by opening an on-off valve disposed in the flow path.

26. A method as in claim 25, wherein the time the valve has been opened is measured and the valve is closed after a preselected period of time has elapsed.

27. A method as in claim 25, wherein the volume of CSF which has been removed is measured and the valve is closed after predetermined volume of removed fluid has been measured.

28. A method as in claim 25, wherein the valve is opened and closed once during each predetermined time period.

29. A method as in claim 28, wherein the valve is opened for a period in the range from 1 hour to 8 hours and provides a flow rate of 0.5 ml/hour to 40 ml/hour.

30. A method as in claim 28, wherein the valve is opened from 2 to $10^8$ times each predetermined period.

31. A method as in claim 30, wherein the valve is opened for a preselected time sufficient to drain a volume of CSF in the range from $10^{-5}$ ml to 40 ml while the valve is open.

32. A method as in claim 19, wherein the flow path is arranged so that the CSF volume removed in any 15-minute period will not exceed 15 ml and in one-hour period will not exceed 50 ml.

33. A method as in claim 19, wherein the flow path modulates flow by filling an accumulator with a predetermined volume of CSF and draining CSF from the accumulator after the accumulator has been filled.

34. A method as in claim 33, wherein the accumulator has a predetermined fill volume in the range from $10^{-5}$ to 40 ml and the accumulator is filled and drained from 1 time to $1.5 \times 10^6$ times during each one-day period.

* * * * *